US00PP14470P39

(12) United States Plant Patent
Hammond

(10) Patent No.: US PP14,470 P3
(45) Date of Patent: Jan. 20, 2004

(54) ARGYRANTHEMUM PLANT NAMED 'M9/18D'

(50) Latin Name: *Argyranthemum frutescens*
Varietal Denomination: M9/18D

(75) Inventor: Francis William Hammond, 100 Boundary Road, Narre Warren East, Victoria 3804 (AU)

(73) Assignee: Francis William Hammond, Victoria (AU)

( * ) Notice: Subject to any disclaimer, the term of this patent is extended or adjusted under 35 U.S.C. 154(b) by 0 days.

(21) Appl. No.: 10/043,948

(22) Filed: Jan. 11, 2002

(65) Prior Publication Data

US 2003/0135904 P1 Jul. 17, 2003

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Susan B. McCormick
(74) *Attorney, Agent, or Firm*—Webb Ziesenheim Logsdon Orkin & Hanson, P.C.

(57) ABSTRACT

A distinct cultivar of Argyranthemum plant named 'M9/18D', characterized by its compact and mounded plant habit; freely branching habit, dense and bushy plants; very freely flowering with numerous inflorescences per plant; red purple colored ray florets that fade to pale pink with age; and yellow disc florets with a red purple centre when immature.

2 Drawing Sheets

BACKGROUND OF THE INVENTION

The present invention relates to a new and distinct cultivar of Agyranthemum plant, botanically known as *Argyranthemum frutescens* and herein after referred to by the name 'M9/18D'.

The new Argyranthemum is a product of a planned breeding program conducted by the inventor in Narre Warren East, Victoria, Australia. The objective of the program is to create and develop new compact Argyranthemum cultivars with numerous inflorescences with attractive floret coloration.

The new Argyranthemum originated from a cross by the inventor of the *Argyranthemum frutescens* cultivar 'M7/02', not patented, as a female, or seed, parent with an unidentified proprietary selection of *Argyranthemum frutescens,* not patented, as the male, or pollen parent. The new Argyranthemum was discovered and selected by the inventor as a plant within the progeny of the stated cross in a controlled environment in Narre Warren East, Victoria, Australia on Aug. 3, 2000. The selection of the new Argyranthemum was based on its compact mounded plant habit, multiple inflorescences and dark red-purple ray florets.

Asexual reproduction of the new Argyranthemum by terminal cutting taken in a controlled environment in Narre Warren East, Victoria, Australia, since Aug. 3, 2000, has shown that the unique features of this new Argyranthemum are stable and reproduced true to type in successive generations.

The new Argyranthemum has not been observed under all possible environmental conditions. The phenotype may vary somewhat with variations in environment such as temperature, day length, light intensity, photoperiod, and water and nutritional status without, however, any variance in genotype.

The following characteristics have been repeatedly observed and are determined to be the basic characteristics of 'M9/18D' and distinguish the new Argyranthemum as a new and distinct cultivar:

(i) compact and mounded plants habit;
(ii) freely branching habit, dense and bushy plants;
(iii) very freely flowering with numerous inflorescences per plant;
(iv) red-purple colored ray florets that fade to pale pink with age;
(v) disc florets with colored yellow with red-purple centres.

Plants of the new Argyranthemum differ from plants of the parent cultivar M7/02 primarily in the size of the plant and ray floret color as plants of the cultivar M7/02 are shorter and narrower and have lighter red-purple colored ray floret. In addition, leaves of the new Argyranthemum are narrower and have apices which are rounded and margins which are crenate whereas plants of cultivar M7/02 have acute apices and margins which are dentate. Plants of the male parent, the unidentified selection of Argeranthemum, differ primarily from plants of the new Argyranthemum in ray floret color.

Plants of the new Argyranthemum are comparable to plants of the cultivar 'M8/20', disclosed in U.S. Plant Pat. No. 13,218. In side-by-side comparisons conducted by the inventor in Narre Warren East, Victoria, Australia, plants of the new Argyranthemum differ from plants of the cultivar 'M8/20' in the following characteristics:

(i) leaves of the new Argyranthemum are narrower than leaves of the cultivar 'M8/20';
(ii) leaves of the new Argyranthemum have rounded apices and crenate leaf margins whereas leaves of 'M8/20' have serrate leaf margins;
(iii) inflorescences of the new leaves of the new Argyranthemum are single in form whereas plants of the cultivar 'M8/20' are semi double in form;
(iv) plants of the new leaves of the new Argyranthemum have darker red-purple florets than the cultivar 'M8/20';

(v) the disc floret array of the new leaves of the new Argyranthemum have red centres which are absent from the disc floret array of 'M8/20'.

BRIEF DESCRIPTION OF THE PHOTOGRAPHS

The accompanying colored photographs illustrate the overall appearance of the new cultivar, showing colors as true as it is reasonably possible to obtain in colored reproductions of this type. Colors in the photographs may differ slightly from the color values cited in the detailed botanical description which accurately describes the colors of the new leaves of the new Argyranthemum. Plants used in the photographs were about 12 weeks from planting rooted cuttings.

DETAILED BOTANICAL DESCRIPTION

Figure 1:
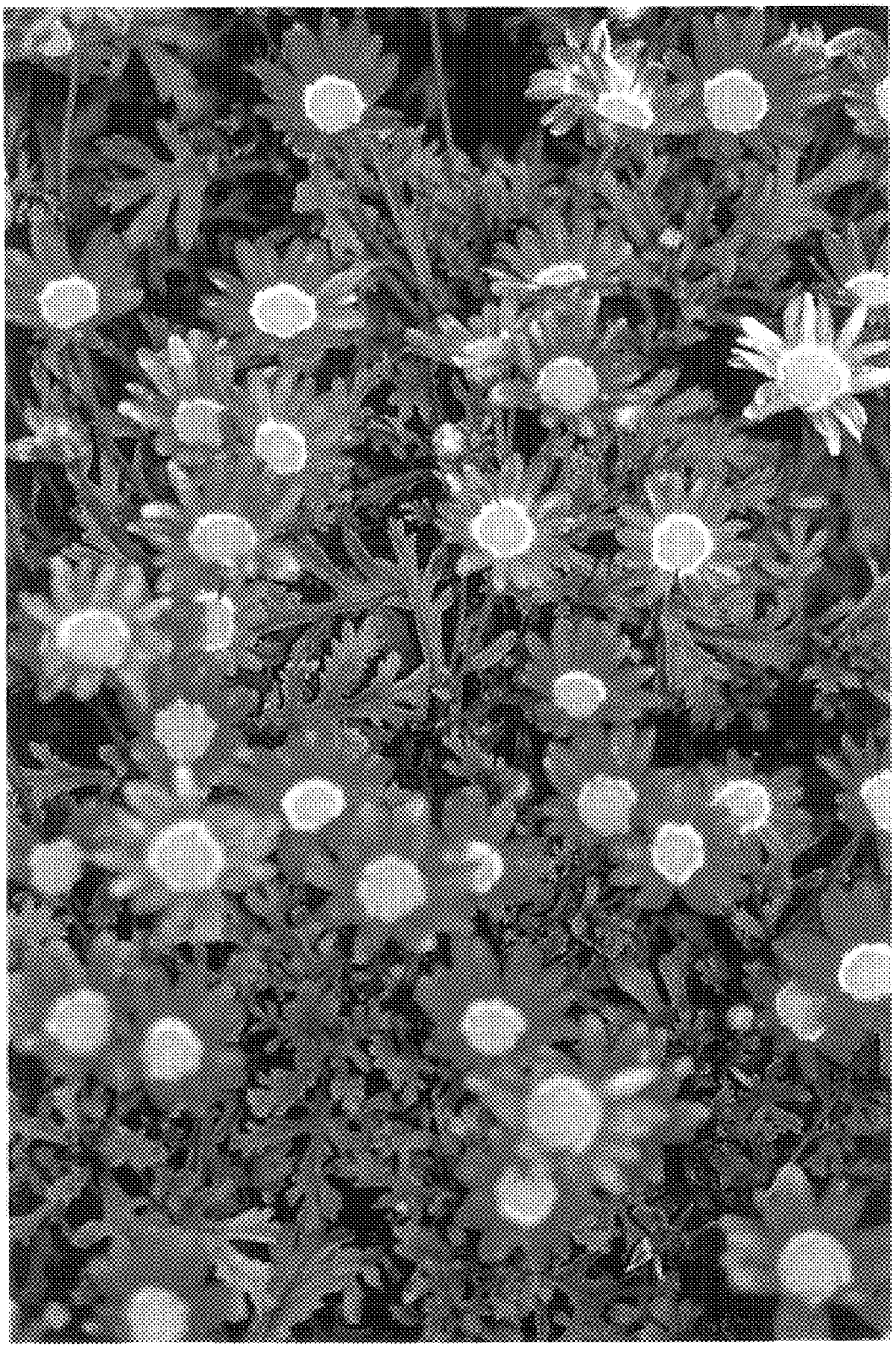
FIG. 1 is a photograph of the plant.
Figure 2:
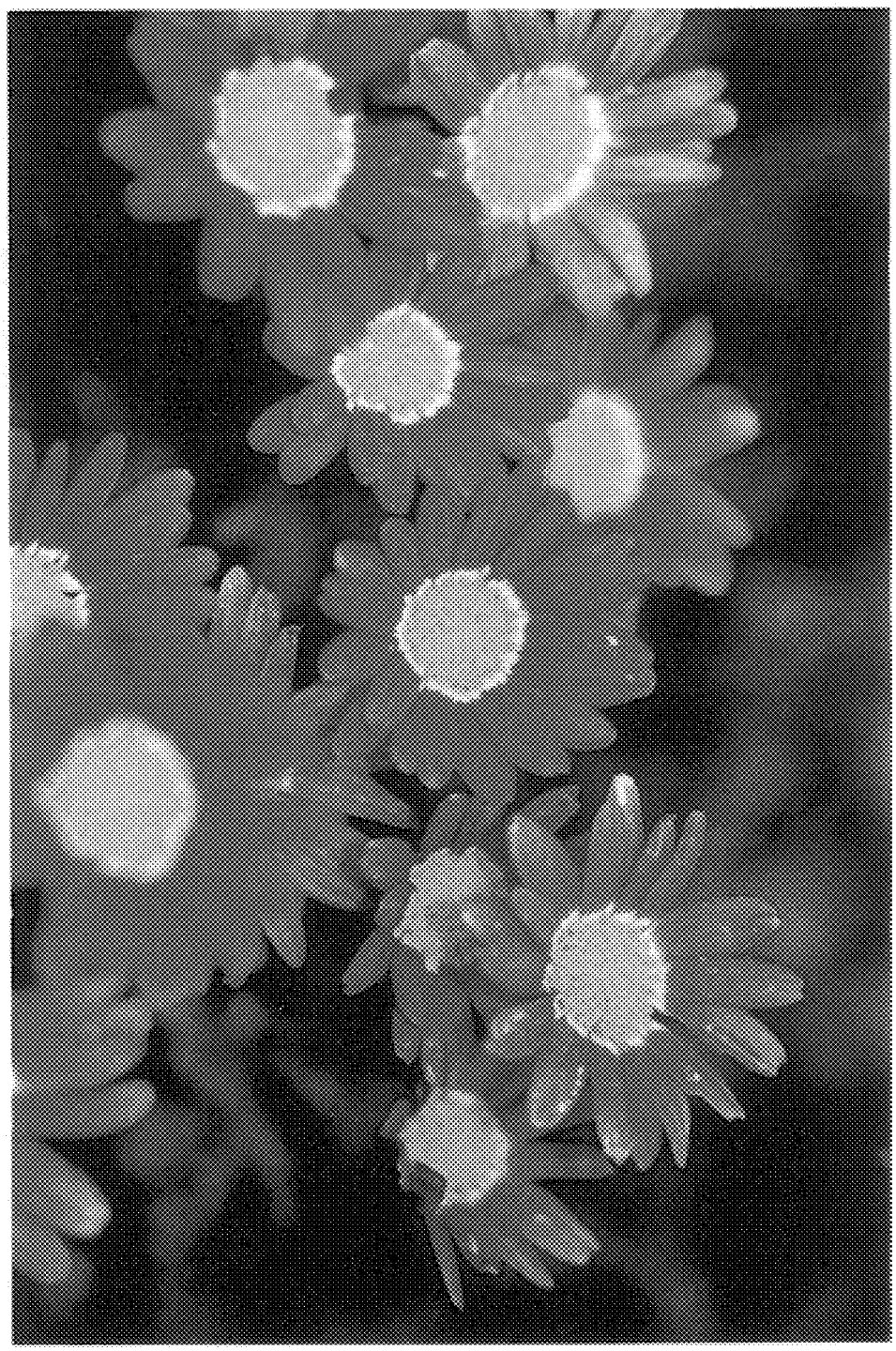
FIG. 2 is a close-up view of the blooms of the new plant.

The following observations, measurements and values describe plants grown at Narre Warren East, Victoria, Australia, under outdoor conditions with day temperatures ranging from 18 to 32° C., night temperatures ranging from 6 to 25° C., and full sunlight. Rooted liners of the new Argyranthemum were planted in 20 cm containers and grown for 12 weeks. Color references are made to The Royal Horticultural Society Colour Chart except where general terms of ordinary dictionary significance are used.

Botanical classification: *Argyranthemum frutescens* cultivar 'M9/18D'.

Parentage:

*Female of seed parent.*—*Argyranthemum frutescens* cultivar 'M7/02', not patented.

*Male of pollen parent.*—Unidentified proprietary selection of *Argyranthemum frutescens,* not patented.

Propagation:

*Type.*—Terminal tip cuttings.

*Time to initiate roots.*—About 7 to 14 days at 22° C.

*Time to produce a rooted cutting.*—About 30 days at 20 to 28° C.

*Root description.*—Fine, fibrous.

Plant description:

*General appearance.*—Compact and bushy growth habit, mounted plant form with dense foliage and inflorescences held about the foliage on long peduncles. Grown in approximately 50 containers having 15 cm to 20 cm diameters.

*Crop time.*—Rapid growth rate; to produce a finished 20 cm containerised plant from rooted cuttings, about 12 weeks are required.

*Plant height.*—About 45 cm.

*Plant width.*—About 50 cm.

*Lateral branch description.*—Quality per plant: about 50. Length: about 12–15 cm. Width: 4 mm. Aspect: mostly upright. Cross-section: round. Texture: smooth, glabrous. Color: 146C.

*Foliage description.*—Arrangement: single, alternative, sessile. Length: about 5 cm. Width: about 3 cm. Shape: Bipinnatifid. Apex: rounded. Base: acuminate. Margin: mostly crenate. Texture, both surfaces: smooth, glabrous. Venation pattern: parallel. Color: Young foliage, upper surface: 143A. Young foliage, lower surface: 143C. Mature foliage, upper surface: 146A. Mature foliage, lower surface: 146B. Venation, upper surface: 144C. Venation, lower surface: 144C.

Inflorescence description:

*Appearance.*—Flat single composite inflorescence form with elliptic shaped ray florets. Inflorescences held upright on axillary peduncles. Disc and ray florets held acropetally on a capitulum. Inflorescences persistent. Inflorescences not fragrant. Inflorescences last about one week on the plant.

*Flowering response.*—Under natural conditions, plants flower from spring to early fall; plants flower continuously during this period.

*Quantity of inflorescences.*—Very freely flowering with about 150 to 160 flower buds and inflorescences per plant.

*Inflorescence size.*—Diameter: up to 5 cm. Depth (height): about 2 cm. Diameter if disc: about 1.5 cm. Receptacle diameter: about 1.4 cm. Receptacle diameter: about 8 mm.

*Flower buds.*—Height: about 8 mm. Diameter: about 8 mm. Shape: roughly spherical. Color: 144B.

*Ray florets.*—Quantity per inflorescence: about 20 in two whorls. Shape: elliptic. Length: about 2 cm. Width: about 5 mm. Apex: emarginate. Base: acute. Margin: entire. Texture, both surfaces: smooth, satiny, glabrous. Aspect: initially upright, when mature, about 90° from the vertical, perpendicular to peduncle. Color: When opening, upper surface: 61A. When opening, lower surface: 60B. Fully opened, upper surface: 61A. Fully opened, lower surface: 78B; fading to 75A with age.

*Disc florets.*—Arrangement: densely massed. Shape: tubular, flared at apex. Color: When immature: 12C with red purple centre. When mature: 13A with red purple specks.

*Peduncle.*—Strength: moderately strong. Aspect: upright. Length: 10 to 12 cm. Diameter: 1.5 mm. Texture: smooth glabrous. Color: 144B.

*Involucral bracts.*—Quantity: about 15. Length: about 5 mm. Width: about 2 mm. Shape: ovate. Apex: acute. Base: cuneate. Margin: entire. Texture, both surfaces: smooth, glabrous. Color: 146C.

*Reproductive organs.*—Androecium: present on disc floret only. Amount of pollen: moderate. Color: HCC4. Gynoecium: present on both ray and disc florets.

*Seed.*—Seed production has not been observed.

Disease resistance: Resistance to pathogens common to Argyranthemum has not been observed on plants grown under commercial conditions.

Temperature/weather tolerance: Plants of the new Argyranthemum have been observed to be tolerant to temperatures as low as −2° C. and temperatures as high as 40° C. Plants of the new Argyranthemum have been observed to be tolerant to rain and wind.

I claim:

1. A new and distinct cultivar of Argyranthemum plant named 'M9/18D' as described and illustrated herein.

* * * * *